United States Patent
Rössler et al.

(10) Patent No.: US 6,372,120 B1
(45) Date of Patent: Apr. 16, 2002

(54) METHOD FOR DETERMINING A NITROGEN OXIDE CONCENTRATION

(75) Inventors: Jürgen Rössler, Münnerstadt; Hong Zhang, Regensburg, both of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/699,600

(22) Filed: Oct. 30, 2000

Related U.S. Application Data

(63) Continuation of application No. PCT/DE99/01090, filed on Apr. 9, 1999.

(30) Foreign Application Priority Data

Apr. 30, 1998 (DE) ......................................... 198 19 581

(51) Int. Cl.$^7$ ............................................. G01N 27/407
(52) U.S. Cl. ..................... 205/781; 204/425; 204/426; 205/784.5
(58) Field of Search ............................... 204/421–429; 205/781, 783–785

(56) References Cited

U.S. PATENT DOCUMENTS 5,928,494 A * 7/1999 Kato et al.
6,059,947 A * 5/2000 Kato et al.

FOREIGN PATENT DOCUMENTS

| EP | 0 769 694 A1 | 4/1997 |
| EP | 0 816 836 A2 | 1/1998 |
| EP | 0 831 322 A2 | 3/1998 |

OTHER PUBLICATIONS

"Thick Film ZrO$_2$ No$_x$ Sensor for the Measurement of Low NOx Concentration" (Kato et al.), Proceedings of the 1998 SAE International Congress & Exposition, Detroit, MI, USA, Feb. 1998.

"Performance of Thick Film NOx Sensor on Diesel and Gasoline Engines" (Kato et al.), Society of Automotive Engineers, 1997. month unavailable.

* cited by examiner

*Primary Examiner*—T. Tung
(74) *Attorney, Agent, or Firm*—Herbert L. Lerner; Laurence A. Greenberg; Werner H. Stemer

(57) ABSTRACT

A NO$_x$ concentration of a gas is measured with a NO$_x$ measuring sensor which has two measuring cells. An oxygen concentration is respectively corrected by a oxygen-ion pumping current. A controller is used for correcting a transitional resistance through which the first oxygen-ion pumping current flows at the first measuring cell, the controller correcting at least partially a correction value for the transitional resistance by using the second oxygen-ion pumping current at the second measuring cell.

5 Claims, 3 Drawing Sheets

METHOD FOR DETERMINING A NITROGEN OXIDE CONCENTRATION

CROSS-REFERENCE TO RELATED APPLICATION

This is a continuation of copending International Application PCT/DE99/01090, filed Apr. 9, 1999, which designated the United States.

BACKGROUND OF THE INVENTION

Field of the Invention:

The invention relates to a method for determining the $NO_x$ concentration in a gas, in particular in the exhaust gas of an internal combustion engine. The concentration is determined with a measuring sensor having a solid electrolyte. The measuring sensor has a first measuring cell, into which the gas passes via a diffusion barrier, in which the oxygen concentration is measured via a first Nernst voltage between a first electrode and a reference electrode, exposed to the ambient air, and is controlled to a first oxygen concentration by means of a first oxygen-ion pumping current between the first electrode and an external electrode. The measured value of the first Nernst voltage is used for controlling the first oxygen-ion pumping current. The sensor further has a second measuring cell, which is connected to the first measuring cell via a diffusion barrier and in which the oxygen concentration is measured via a second Nernst voltage between a second electrode and the reference electrode and is controlled to a second oxygen concentration by means of a second oxygen-ion pumping current (Ip1) between the second electrode and the external electrode. The $NO_x$ concentration is measured at the same time by a measuring electrode in the second measuring cell.

For measuring the $NO_x$ concentration in a gas, for example in the exhaust gas of an internal combustion engine, it is known to use a thick-film measuring sensor. Such a measuring sensor is described in the publication by N. Kato et al., "Performance of Thick Film $NO_x$ Sensor on Diesel and Gasoline Engines," Society of Automotive Engineers, publication 970858, 1997, or in N. Kato et al., "Thick Film $NO_x$ Sensor for the Measurement of Low $No_x$ Concentration", Society of Automotive Engineers, publication 98D170, 1998. That measuring sensor has two measuring cells and consists of a zirconium oxide that conducts oxygen ions. The system implements the following measuring concept: in a first measuring cell, which is fed the gas to be measured via a diffusion barrier, a first oxygen concentration is set by means of a first oxygen-ion pumping current, with no decomposition of $NO_x$ taking place. In a second measuring cell, which is connected to the first measuring cell via a diffusion barrier, the oxygen content is further reduced by means of a second oxygen-ion pumping current and $NO_x$ decomposes at a measuring electrode. The oxygen generated in this way is sensed as a measure of the $NO_x$ concentration. The entire measuring sensor is in this case brought to an elevated temperature, for example 430° C., by means of an electric heater. The measuring error of the measuring sensor described in the publication corresponds to an $NO_x$ concentration of 22 ppm.

The measuring error is of a systematic nature for the MO following reasons: for setting the first oxygen concentration in the first measuring cell, the oxygen-ion pumping current Ip0 flows between a first electrode and an external electrode through the thick-film material, which in this case is a solid electrolyte of $ZrO_2$. Between the solid electrolyte $ZrO_2$ and the first electrode there is a transitional resistance R, through which the oxygen-ion pumping current Ip0 flows. The resultant voltage drop is measured at the same time as the determination of a first Nernst voltage V0 in the first measuring cell, which is used for controlling the first oxygen-ion pumping current Ip0. The measured voltage V0 thus comprises the actual Nernst voltage $V_{NO}$ and the described additive voltage drop across the transitional resistance R0. This makes it more difficult for controlling to the first oxygen concentration to be carried out in the first measuring cell and leads to a systematic error, since too low a first oxygen concentration may under certain circumstances cause $NO_x$ that was actually intended to be decomposed and measured only in the second measuring cell to be decomposed already at the first electrode. If the first oxygen concentration is too high, too much oxygen diffuses into the second measuring cell, in which the residual oxygen content becomes too high as a result. This likewise leads to a falsification of the $NO_x$ measurement.

In the prior art, this problem has been solved by using the fact that, with an ideally set first oxygen concentration at the first measuring cell, the setpoint value for the second oxygen-ion pumping current Ip1, with which the second oxygen content in the second measuring cell is set, is known. This setpoint value for the second oxygen-ion pumping current Ip1 can then be used for correcting the measured value V0 of the first Nernst voltage to the extent that the second oxygen-ion pumping current Ip1 achieves this setpoint value. The control required for this cannot, however, be designed to be very fast, for reasons of stability, so that when there are rapid changes in $NO_x$ concentration in the gas to be measured compensation is not completely possible. Then the first oxygen concentration in the first measuring cell is not controlled to the desired value, which, as described, leads to measuring errors in the sensing of the $NO_x$ concentration.

It has become known from U.S. Pat. No. 6,036,842 (see Japanese application JP 170160/96 and European published application EP 0 816 836 A2) to incorporate a voltage derived from the first pumping current into the control of the first pumping current for correcting a transitional resistance.

SUMMARY OF THE INVENTION

The object of the invention is to provide a method for determining a $NO_x$ concentration in a gas which overcomes the above-noted deficiencies and disadvantages of the prior art devices and methods of this kind, and which allows a more exact sensing and measurement of the $NO_x$ concentration in a gas using the above-described measuring sensor.

With the above and other objects in view there is provided, in accordance with the invention, a method of determining a $NO_x$ concentration in a gas, in particular in an exhaust gas of an internal combustion engine. The method comprises:

providing a measuring sensor with a solid electrolyte, a first measuring cell with a first electrode, a second measuring cell with a second electrode, a diffusion barrier separating the first measuring cell from the second measuring cell, and a reference electrode exposed to ambient air;

allowing a gas to pass via a diffusion barrier into the first measuring cell, measuring an oxygen concentration in the first measuring cell via a first Nernst voltage between the first electrode and the reference electrode, and regulating the oxygen concentration to a first oxygen concentration with a first oxygen-ion pumping current between the first electrode and an external electrode, and thereby using a measured value of the first Nernst voltage for controlling the first oxygen-ion pumping current;

measuring an oxygen concentration in the second measuring cell via a second Nernst voltage between the second electrode and the reference electrode, and regulating the oxygen concentration in the second measuring cell to a second oxygen concentration with a second oxygen-ion pumping current between the second electrode and the external electrode;

also measuring the $NO_x$ concentration with a measuring electrode in the second measuring cell; and correcting an error occurring in a setting of the first oxygen-ion pumping current by correcting the measured value of the first Nernst voltage with a product of a correction value and the first oxygen-ion pumping current, wherein the correction value approximates a transitional resistance between the first electrode and the solid electrolyte being supplied at least partially by a controller, wherein the controller uses as a reference variable a prescribed value ($Ip1_{set}$) of the second oxygen-ion pumping current and as a controlled variable a current value of the second oxygen-ion pumping current.

In other words, the measured value V0 of the first Nernst voltage is corrected by a controller, which uses as the reference variable a setpoint value $Ip1_{set}$ of the second oxygen-ion pumping current and as the controlled variable the current value of the second oxygen-ion pumping current Ip1 and, as a result, approximates the transitional resistance R0 at least partially by a correction value R0'. Since the transitional resistance R0 is subjected to only slowly changing influences—to be mentioned here in particular are the temperature of the measuring sensor, the temperature of the gas to be measured or the mass flow of the gas to be measured—this controller can be designed in such a way that it operates only very slowly, and as a result is very exact. The voltage drop, falsely measured at the same time as the determination of the first Nernst voltage $U_{NO}$, across the transitional resistance R0 between the solid electrolyte and the first electrode can then be corrected by the product of the correction value R0' and the current Ip0, since the first oxygen-ion pumping current Ip0 is known.

The advantage of this procedure is that an exact correction of the measured value V0 for the first Nernst voltage is now possible even when there are rapid dynamic changes in the gas to be measured, since there is a single correction value R0' of the resistance R0 for the various operating states. After all, the correction value R0' for the resistance is used only to compensate for a slow change. Consequently, the accuracy of measuring the $NO_x$ concentration is increased.

In accordance with an added feature of the invention, an approximation of the transitional resistance by the correction value is partly supplied with the controller and partly taken from a characteristic map that depends on at least one of the following variables: a temperature of the measuring sensor, a temperature of the gas to be measured, and/or a mass flow of the gas to be measured.

In accordance with an additional feature of the invention, the transitional resistance is shifted by a correction value composed of a constant value and a value supplied by the controller.

In accordance with a concomitant feature of the invention, the constant value is assumed only if the temperature of the second measuring cell and the temperature of the first measuring cell are substantially equal.

Other features which are considered as characteristic for the invention are set forth in the appended claims.

Although the invention is illustrated and described herein as embodied in a method for determining $NO_x$ concentration, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
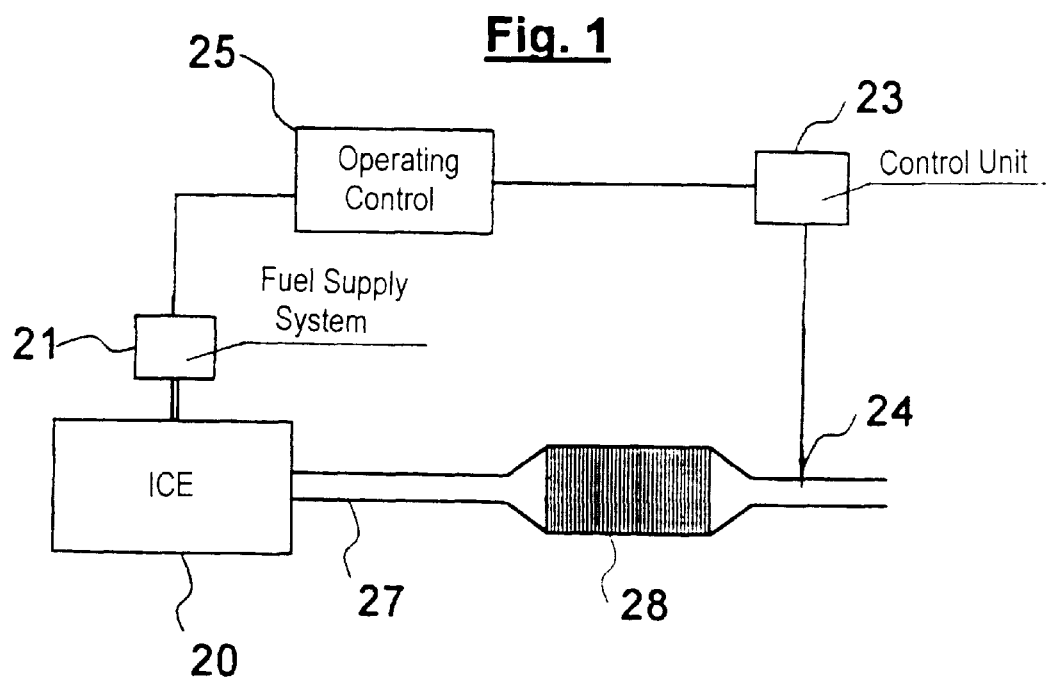
FIG. 1 is a schematic block diagram of a device for carrying out the method according to the invention.
Figure 2:
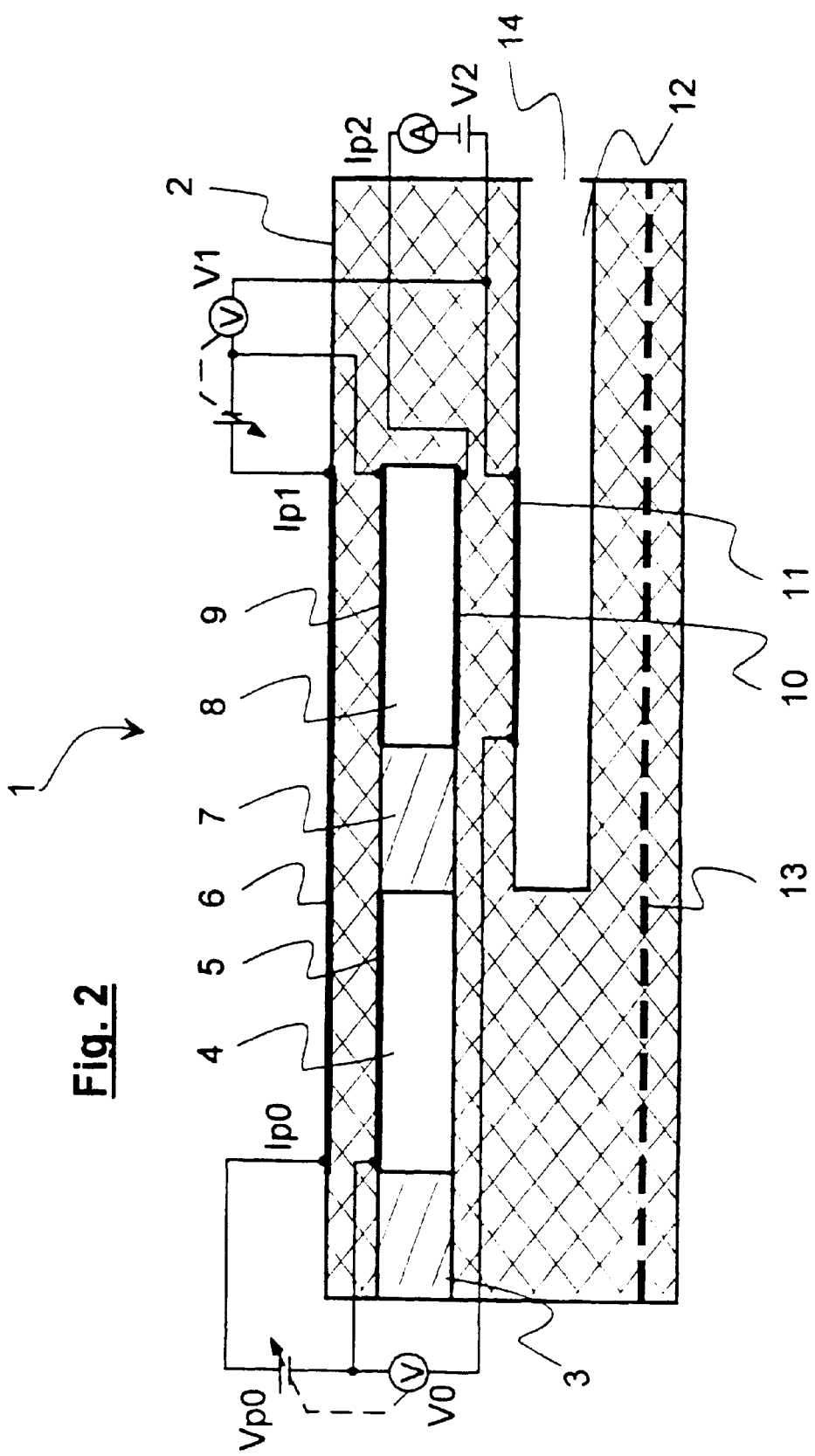
FIG. 2 is a schematic sectional representation of a measuring sensor with which the method according to the invention is carried out.

Referring now to the figures of the drawing in detail, FIG. 2 illustrates a schematic of a section through an $NO_x$ measuring sensor 1. The measuring sensor 1 is used as measuring sensor 24 in the device represented in FIG. 1 for determining the $NO_x$ concentration in the exhaust system 27 of an internal combustion engine 20. The $NO_x$ measuring sensor 24 is operated by a control unit 23, which is connected to the $NO_x$ measuring sensor 24 and carries out the control processes necessary for the operation of the $NO_x$ measuring sensor 24. The measured value of the $NO_x$ concentration supplied by the control unit 23 is fed via a bidirectional, digital interface to an operating control device 25 of the internal combustion engine 20, which activates a fuel supply system 21 of the internal combustion engine 20 in such a way that an $NO_x$-reducing catalyst 28, which in this case lies upstream of the $NO_x$ measuring sensor 24 in the exhaust system 27, has optimum operating characteristics.

The measuring sensor 24, is represented in a more detailed form in FIG. 2, where it is identified with numeral 1. The control processes taking place during the operation of the $NO_x$ measuring sensor 1 are schematically illustrated in the block diagram of FIG. 3. The measuring sensor 1 comprising a solid electrolyte 2, in this case $ZrO_2$, takes up the exhaust gas to be measured, which has an $NO_x$ concentration conc0, via a diffusion barrier 3. The exhaust gas diffuses through the diffusion barrier 3 into a first measuring cell 4. The oxygen content in the first measuring cell is measured by means of a first Nernst voltage V0 between a first electrode 5 and a reference electrode 11, exposed to ambient air. In this case, the reference electrode 11 is arranged in an air duct 12, into which ambient air enters via an opening 14. Both electrodes 5, 11, are conventional platinum electrodes.

Figure 3:
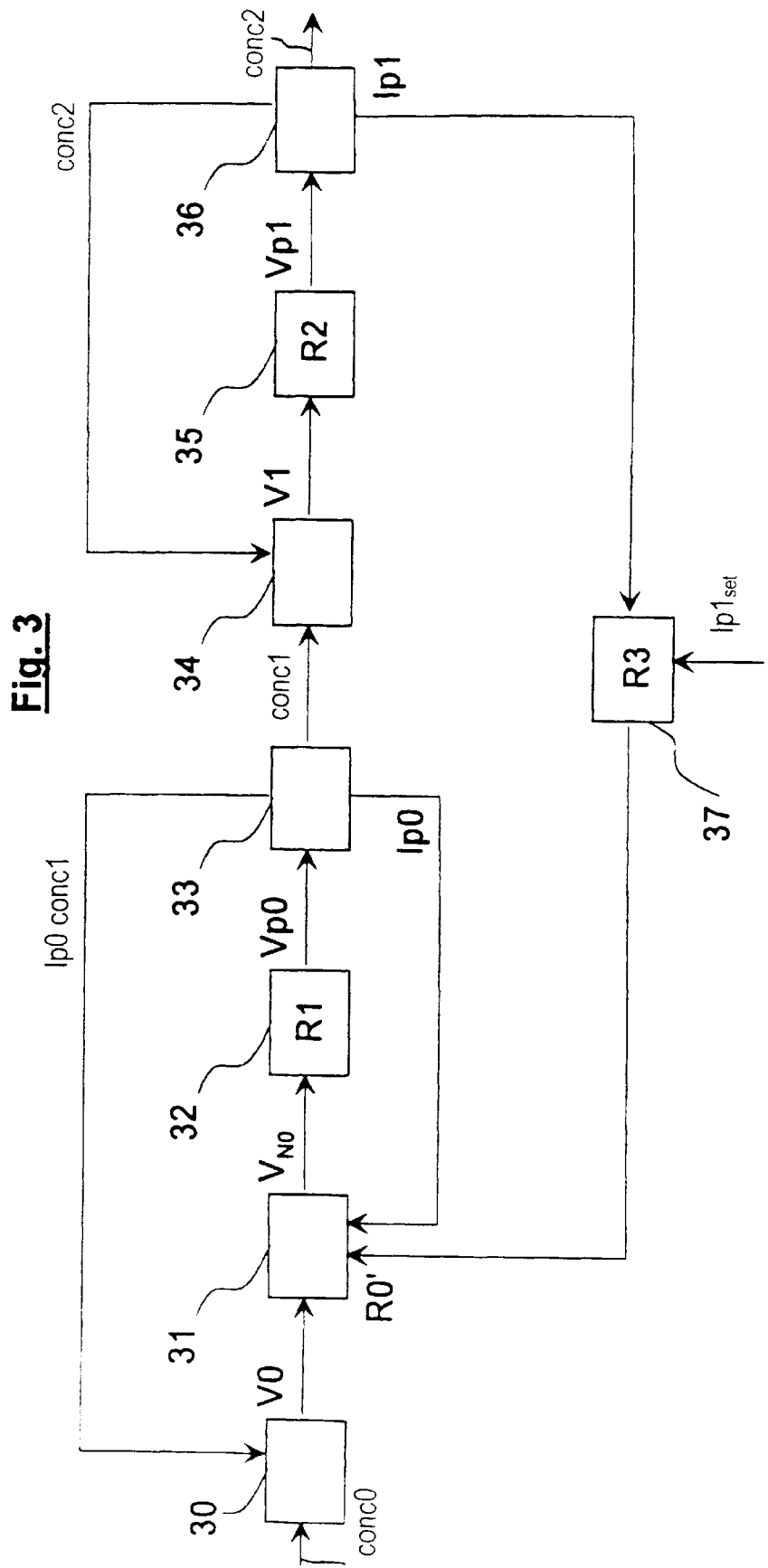
FIG. 3 is a block diagram illustrating the control processes taking place when the method is carried out.

In the conventional method, the measured value of the first Nernst voltage V0 is used for setting a first control voltage Vp0, which is indicated in FIG. 3 by a block 30. The control voltage Vp0 drives a first oxygen-ion pumping current Ip0 through the solid electrolyte 2 of the measuring sensor 1 between the first electrode 5 and an external electrode 6 (block 33 in FIG. 3). The control voltage Vp0 is thereby set by a controller R1 in such a way that there is a predetermined oxygen concentration conc1 in the first measuring cell 4 (block 32).

The first measuring cell 4 is connected to a second measuring cell 8 via a further diffusion barrier 7. The gas present in the measuring cell 4 diffuses through this diffusion barrier 7 into the second measuring cell. The second oxygen concentration in the second measuring cell 8 is measured via a second Nernst voltage V1 between a second electrode 9, which is likewise a platinum electrode, and the reference electrode 11 (block 34) and is used by a controller R2 (block 35) for prescribing a second control voltage Vp1, which drives a second oxygen-ion pumping current Ip1 (block 36). The second oxygen-ion pumping current Ip1 from the second measuring cell flows from the second electrode 9 through the solid electrolyte 2 to the external electrode 6. With the aid of this current, a predetermined oxygen concentration conc2 is set in the second measuring cell 8 (output block 36).

The $NO_x$ not affected by the previous processes in the measuring cells 4 and 8 is then decomposed at the measuring electrode 10, which is formed in such a way that it is catalytically active, by applying a voltage V2 between the measuring electrode 10 and the reference electrode 11, and the released oxygen is pumped through the solid electrolyte 2 in a third oxygen-ion pumping current Ip2 toward the reference electrode 11. If there is a sufficiently small residual oxygen content in the measuring cell 8, the third oxygen-ion pumping current Ip2 is carried only by oxygen ions which originate from the decomposition of $NO_x$. That current is consequently a measure of the $NO_x$ concentration in the measuring cell 8 and consequently in the exhaust gas to be measured.

For controlling the first oxygen-ion pumping current Ip0 by the controller R1 (block 32), according to the prior art the measured value V0 of the first Nernst voltage is used directly. However, as already described, that value is falsified by a voltage drop across a transitional resistance R0 between the solid electrolyte 2 and the first electrode 5, since the resistance R0 is traversed by the first oxygen-ion pumping current Ip0.

According to the invention, therefore, the measured value V0 of the first Nernst voltage is corrected in advance with respect to the actual Nernst voltage $V_{NO}$ (block 31), in that a value R0' supplied by a controller R3 (block 37) for the resistance R0 is multiplied by the first oxygen-ion pumping current Ip0 and the falsifying voltage drop is calculated from this. The controller R3 receives as the reference variable the setpoint value $Ip1_{set}$ of the second oxygen-ion pumping current Ip1 which would occur if the first oxygen concentration had been ideally corrected in the first measuring cell 4. Any deviation is of course caused by the voltage drop across the resistance R0. The controller R3 can in this case be designed to operate very slowly, since it is intended to follow only changes of the transitional resistance R0 itself, which are independent of, for example, changes in the initial $NO_x$ concentration conc0.

The controller R3 advantageously provides only part of the correction value R0'; the other part, which may be combined multiplicatively or additively with the part supplied by the controller R3, originates from a characteristic map, which depends on the exhaust-gas temperature, the measuring-sensor temperature and the exhaust-gas mass flow, although not all dependences have to be applied in practice. If the temperature of the first measuring cell 4 is equal to that of the second measuring cell 8, the exhaust-gas mass flow is no longer relevant and the part supplied by the controller R3 for forming the correction value R0' can be combined, for example, with a constant value.

The advantage of this procedure is that an exact correction of the measured value V0 of the first Nernst voltage is possible even when there are rapid dynamic changes in the $NO_x$ concentration in the exhaust gas. Since the controller R3 can be designed to operate slowly, it is of no relevance to the stability aspect of designing the controller system.

We claim:

1. A method of determining a $NO_x$ concentration in a gas, which comprises:
    providing a measuring sensor with a solid electrolyte, a first measuring cell with a first electrode, a second measuring cell with a second electrode, a diffusion barrier separating the first measuring cell from the second measuring cell, an exterior electrode, and a reference elect rode exposed to ambient air;
    connecting a first controller to the first electrode and the external electrode for controlling a current therebetween;
    connecting a second controller to the second electrode and the external electrode for controlling a current therebetween;
    allowing a gas to pass via a diffusion barrier into the first measuring cell, measuring an oxygen concentration in the first measuring cell via a first Nernst voltage between the first electrode and the reference electrode, and regulating the oxygen concentration to a first oxygen concentration with a first oxygen-ion pumping current between the first electrode and the external electrode with the first controller by using a measured value of the first Nernst voltage for controlling the first oxygen-ion pumping current;
    measuring an oxygen concentration in the second measuring cell via a second Nernst voltage between the second electrode and the reference electrode, and regulating the oxygen concentration in the second measuring cell to a second oxygen concentration with a second oxygen-ion pumping current between the second electrode and the external electrode with the second controller;
    also measuring the $NO_x$ concentration with a measuring electrode in the second measuring cell; and
    correcting an error occurring in the measured value of the first Nernst voltage due to a transitional resistance between the first electrode and the solid electrolyte by the following steps:
        providing a third controller using a prescribed value of the second oxygen-ion pumping current as a reference variable and a current value of the second oxygen-ion pumping current in order to provide a correction value approximating the transitional resistance at least partially as a controlled variable;
        multiplying the correction value and the first oxygen-ion pumping current to provide a product value; and
        using the product value to correct the measured value of the first Nernst voltage.

2. The method according to claim 1, which comprises partly supplying an approximation of the transitional resistance by the correction value with the third controller and partly taking from a characteristic map that depends on at least one variable selected from the group of variables consisting of a temperature of the measuring sensor, a temperature of the gas to be measured, and a mass flow of the gas to be measured.

3. The method according to claim 1, which comprises shifting the transitional resistance by a correction value composed of a constant value and a value supplied by the third controller.

4. The method according to claim 3, which comprises assuming the constant value only if the temperature of the second measuring cell and the temperature of the first measuring cell are substantially equal.

5. The method according to claim 1, which comprises exposing the measuring sensor to an exhaust gas of an internal combustion engine and measuring the $NO_x$ concentration in the exhaust gas.

* * * * *